(12) United States Patent
Mobley

(10) Patent No.: US 7,923,001 B2
(45) Date of Patent: Apr. 12, 2011

(54) COMPOSITIONS AND METHODS FOR DIAGNOSING AND TREATING URINARY TRACT INFECTIONS

(75) Inventor: Harry L. T. Mobley, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 12/204,966

(22) Filed: Sep. 5, 2008

(65) Prior Publication Data

US 2009/0068220 A1    Mar. 12, 2009

Related U.S. Application Data

(60) Provisional application No. 60/970,661, filed on Sep. 7, 2007.

(51) Int. Cl.
*A61K 49/00* (2006.01)
*A61K 39/00* (2006.01)
*A61K 39/108* (2006.01)

(52) U.S. Cl. ..... 424/9.2; 424/9.1; 424/184.1; 424/185.1; 424/234.1; 424/241.1

(58) Field of Classification Search ......... None
See application file for complete search history.

(56) References Cited

U.S. PATENT DOCUMENTS

| | | |
|---|---|---|
| 4,578,770 A | 3/1986 | Mitani |
| 4,596,792 A | 6/1986 | Vyas |
| 4,599,230 A | 7/1986 | Milich et al. |
| 4,599,321 A | 7/1986 | Rainis |
| 4,601,903 A | 7/1986 | Frasch |
| 4,608,251 A | 8/1986 | Mia |
| 7,208,574 B1 | 4/2007 | Finlay et al. |
| 2002/0115829 A1 | 8/2002 | Finlay et al. |

OTHER PUBLICATIONS

PCT International Search Report; PCT International Patent Application No. PCT/US2008/075329; Applicants: Mobley, Harry L.T., et al., filed Sep. 5, 2008 (4 pgs.).
Hagan, E.C. Mobley, H.L. "Uropathogenic *Escherichia coli* Outer membrane Antigens Expressed during Urinary Tract Infection," Infect Immun. Aug. 2007, vol. 75, No. 8, pp. 3941-3949.
Mobley, et al., 1993. "Isogenic P-fimbrial deletion mutants of pyelonephritogenic *Escherichia coli*: the role of alpha Gal(1-4) beta Gal binding in virulence of a wild-type strain." Molecular Microbiology 10:143-55.
Mobley, et al. "Pyelonephritogenic *Escherichia coli* and Killing of Cultured Human Renal Proximal Tubular Epithelial Cells:Role of Hemolysin in Some Strains"1990. Infection & Immunity 58:1281-9.
Welch, et al., "Extensive mosaic structure revealed by the complete genome sequence of uropathogenic *Escherichia coli*" 2002. Proceedings of the National Academy of Sciences of the United States of America 99:17020-4.
Stapleton, et al., "Urovirulence determinant in *Escherichia coli* isolates causing first-episode and recurrent cystitis in women." 1991. Journal of Infectious Diseases 163:773-9.
Blattner, et al.; "The complete genome sequence of *Escherichia coli* K-12." 1997, Science 277:1453-74.
Parkhill, et al., "Genome sequence of *Yersinia pestis*, the causative agent of plague" 2001. Nature 413:523-7.
Heimer, et al., "Autotransporter Genes pic and tsh Are Associated with *Escherichia coli* Strains That Cause Acute Pyelonephritis and Are Expresses during Urinary Tract Infection"2004. Infect Immun 72:593-7.

*Primary Examiner* — Rodney P. Swartz
(74) *Attorney, Agent, or Firm* — Casimir Jones, S.C.

(57) ABSTRACT

The present invention relates to methods and compositions for treating urinary tract infections. In particular, the present invention relates to vaccines and immune modulators for treating urinary tract infections.

18 Claims, 13 Drawing Sheets

Clone and express proteins with C-terminal His₆ tag

Nickel-nitriloacetic acid column purification

Pool fractions and buffer exchange

Purified protein

COMPOSITIONS AND METHODS FOR DIAGNOSING AND TREATING URINARY TRACT INFECTIONS

This application claims priority to provisional application 60/970,661, filed Sep. 7, 2007, which is herein incorporated by reference in its entirety.

This invention was made with government support under grant number 2 R01 AI043363 awarded by the National Institutes of Health. The government has certain rights in the invention.

FIELD OF THE INVENTION

The present invention relates to methods and compositions for treating urinary tract infections. In particular, the present invention relates to vaccines and immune modulators for treating urinary tract infections.

BACKGROUND OF THE INVENTION

A urinary tract infection (UTI) is an infection that begins in the urinary system. Serious consequences can occur if the infection spreads to the kidneys. Women are most at risk of developing a UTI. In fact, half of all women will develop a UTI during their lifetimes, and many will experience more than one. When treated promptly and properly, UTIs rarely lead to complications. But left untreated, a urinary tract infection can become something more serious than a set of uncomfortable symptoms. Untreated UTIs can lead to acute or chronic kidney infections (pyelonephritis), which could permanently damage kidneys. Young children and older adults are at the greatest risk of kidney damage due to UTIs because their symptoms are often overlooked or mistaken for other conditions. Women who have UTIs while pregnant may also have an increased risk of delivering low birth weight or premature infants.

UTIs are generally treated with antibiotics as a first line of treatment. Drugs most commonly recommended for simple UTIs include amoxicillin (Amoxil, Trimox), nitrofurantoin (Furadantin, Macrodantin), trimethoprim (Proloprim) and the antibiotic combination of trimethoprim and sulfamethoxazole (Bactrim, Septra). For severe UTIs, hospitalization and treatment with intravenous antibiotics may be necessary. However, many antibiotic resistant bacteria are present in the environment, especially in hospital and other health care settings. Thus, additional treatments for UTIs are needed.

SUMMARY OF THE INVENTION

The present invention relates to methods and compositions for treating urinary tract infections. In particular, the present invention relates to vaccines and immune modulators for treating urinary tract infections.

For example, in some embodiments, the present invention provides a method of inducing an immune response, comprising administering a composition comprising an effective amount of at least a portion of one or more antigens (e.g., including, but not limited to, ChuA, c2482, Iha, IroN, IutA, and IreA) to a subject under conditions such that the subject generates an immune response to a bacteria (e.g., E. coli) in the subjects urinary tract. In some embodiments, the composition further comprises an adjuvant (e.g., cholera toxin). In some embodiments, the cholera toxin is crosslinked to the antigen. In some embodiments, at least a portion is a peptide that corresponds to extracellular loop 7 of IroN or loop 6 of IutA. In some embodiments, the immune response protects the subject from developing symptoms of a urinary tract infection. In some embodiments, the subject exhibits decreased levels of bacteria in their bladder or kidney.

The present invention further provides a method of preventing urinary tract infections in a subject, comprising administering a composition comprising an effective amount of one or more antigens (e.g., including, but not limited to, ChuA, c2482, Iha, IroN, IutA, and IreA) to a subject under conditions such that the subject does not develop symptoms of a urinary tract infection.

The present invention additionally provides vaccine compositions comprising the antigens described herein, as well as kit comprising the vaccine and any other components necessary, sufficient or useful for administering the vaccine (e.g., including, but not limited to, administration devices (e.g., needles, etc.), instructions, sanitation components, temperature components, adjuvants and the like).

Additional embodiments of the invention are described in the below description and accompanying drawings.

DEFINITIONS

Figure 1:
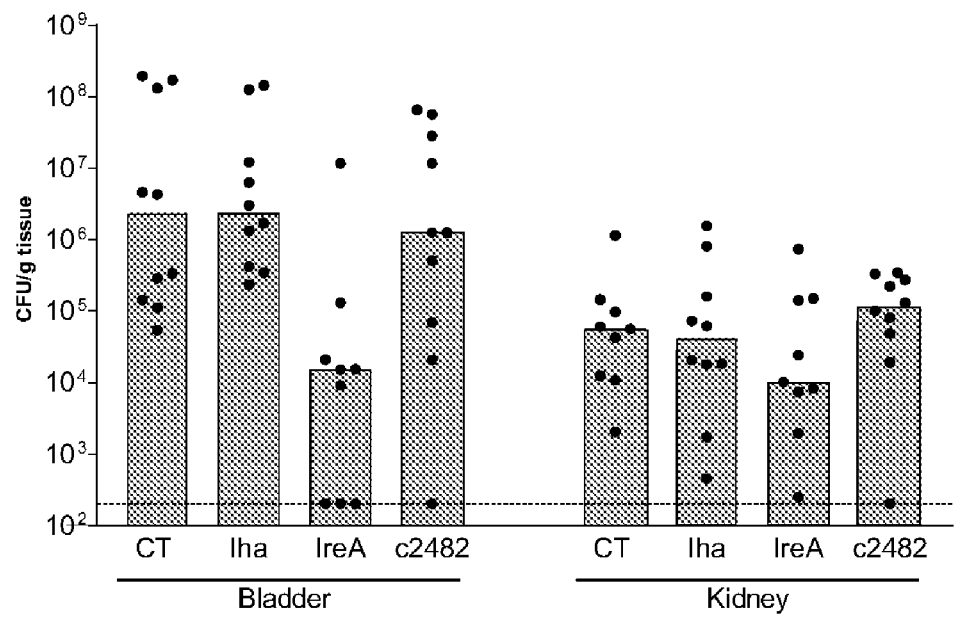
FIG. 1 shows colony forming units of E. coli following treatment with (A) 30 µg or (B) 100 µg of purified antigen (Ag) crosslinked to cholera toxin (CT), followed by two 10 µg boosts at one-week intervals.
Figure 1:
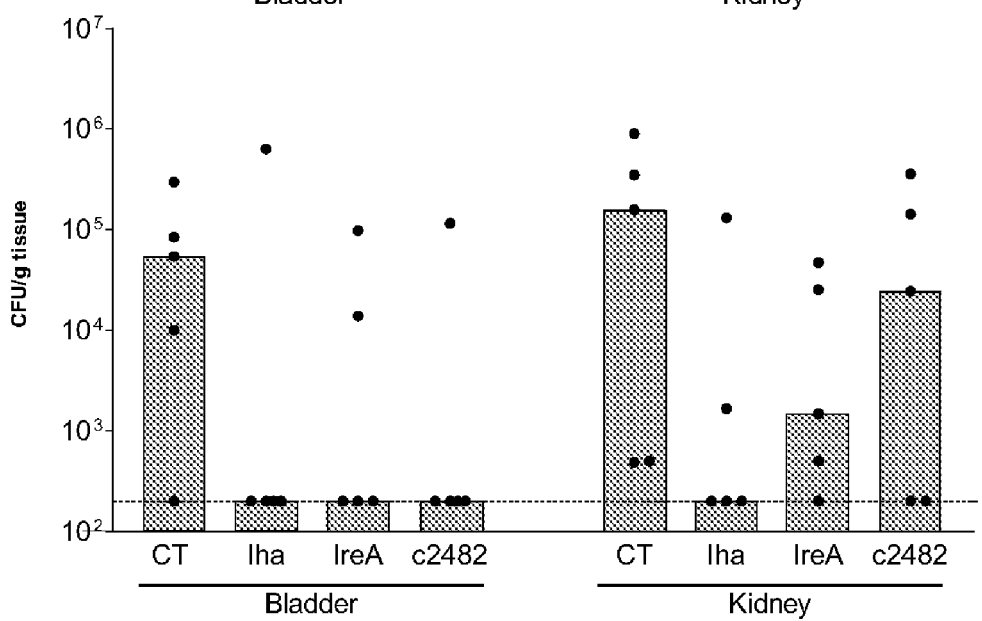

To facilitate understanding of the invention, a number of terms are defined below.

Where "amino acid sequence" is recited herein to refer to an amino acid sequence of a naturally occurring protein molecule, "amino acid sequence" and like terms, such as "polypeptide" or "protein" are not meant to limit the amino acid sequence to the complete, native amino acid sequence associated with the recited protein molecule.

As used herein, the term "peptide" refers to a polymer of two or more amino acids joined via peptide bonds or modified peptide bonds. As used herein, the term "dipeptides" refers to a polymer of two amino acids joined via a peptide or modified peptide bond.

The term "wild-type" refers to a gene or gene product that has the characteristics of that gene or gene product when isolated from a naturally occurring source. A wild-type gene is that which is most frequently observed in a population and is thus arbitrarily designed the "normal" or "wild-type" form of the gene. In contrast, the terms "modified", "mutant", and "variant" refer to a gene or gene product that displays modifications in sequence and or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "fragment" as used herein refers to a polypeptide that has an amino-terminal and/or carboxy-terminal deletion as compared to the native protein, but where the remaining amino acid sequence is identical to the corresponding positions in the amino acid sequence deduced from a full-length cDNA sequence. Fragments typically are at least 4 amino acids long, preferably at least 20 amino acids long, usually at least 50 amino acids long or longer, and span the portion of the polypeptide required for intermolecular binding of the compositions with its various ligands and/or substrates.

As used herein, the term "purified" or "to purify" refers to the removal of contaminants from a sample. For example, antigens are purified by removal of contaminating proteins. The removal of contaminants results in an increase in the percent of antigen (e.g., antigen of the present invention) in the sample.

The term "recombinant DNA molecule" as used herein refers to a DNA molecule that is comprised of segments of DNA joined together by means of molecular biological techniques.

The term "recombinant protein" or "recombinant polypeptide" as used herein refers to a protein molecule that is expressed from a recombinant DNA molecule.

The term "native protein" as used herein to indicate that a protein does not contain amino acid residues encoded by vector sequences; that is the native protein contains only those amino acids found in the protein as it occurs in nature. A native protein may be produced by recombinant means or may be isolated from a naturally occurring source.

As used herein the term "portion" when in reference to a protein (as in "a portion of a given protein") refers to fragments of that protein. The fragments may range in size from four consecutive amino acid residues to the entire amino acid sequence minus one amino acid.

The term "Western blot" refers to the analysis of protein(s) (or polypeptides) immobilized onto a support such as nitrocellulose or a membrane. The proteins are run on acrylamide gels to separate the proteins, followed by transfer of the protein from the gel to a solid support, such as nitrocellulose or a nylon membrane. The immobilized proteins are then exposed to antibodies with reactivity against an antigen of interest. The binding of the antibodies may be detected by various methods, including the use of radiolabelled antibodies.

The term "antigenic determinant" as used herein refers to that portion of an antigen that makes contact with a particular antibody (i.e., an epitope). When a protein or fragment of a protein is used to immunize a host animal, numerous regions of the protein may induce the production of antibodies that bind specifically to a given region or three-dimensional structure on the protein; these regions or structures are referred to as antigenic determinants. An antigenic determinant may compete with the intact antigen (i.e., the "immunogen" used to elicit the immune response) for binding to an antibody.

As used herein, the term "host cell" refers to any eukaryotic or prokaryotic cell (e.g., bacterial cells such as *E. coli*, yeast cells, mammalian cells, avian cells, amphibian cells, plant cells, fish cells, and insect cells), whether located in vitro or in vivo. For example, host cells may be located in a transgenic animal.

The term "test compound" refers to any chemical entity, pharmaceutical, drug, and the like that can be used to treat or prevent a disease, illness, sickness, or disorder of bodily function, or otherwise alter the physiological or cellular status of a sample. Test compounds comprise both known and potential therapeutic compounds. A test compound can be determined to be therapeutic by screening using the screening methods of the present invention. A "known therapeutic compound" refers to a therapeutic compound that has been shown (e.g., through animal trials or prior experience with administration to humans) to be effective in such treatment or prevention.

The term "sample" as used herein is used in its broadest sense. As used herein, the term "sample" is used in its broadest sense. In one sense it can refer to a tissue sample. In another sense, it is meant to include a specimen or culture obtained from any source, as well as biological. Biological samples may be obtained from animals (including humans) and encompass fluids, solids, tissues, and gases. Biological samples include, but are not limited to blood products, such as plasma, serum and the like. These examples are not to be construed as limiting the sample types applicable to the present invention. A sample suspected of containing a human chromosome or sequences associated with a human chromosome may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

DETAILED DESCRIPTION OF THE INVENTION

The present invention relates to methods and compositions for treating urinary tract infections. In particular, the present invention relates to vaccines and immune modulators for treating urinary tract infections.

Uropathogenic *Escherichia coli* (UPEC) are responsible for the majority of uncomplicated urinary tract infections, which can present clinically as cystitis or pyelonephritis. UPEC strain CFT073, isolated from the blood of a patient with acute pyelonephritis, is a highly cytotoxic and virulent strain. Experiments conducted during the course of development of embodiments of the present invention used the genome sequence of CFT073 to generate microarrays for comparative genomic hybridization (CGH) analysis of uropathogenic and fecal/commensal *E. coli* isolates. Genomic DNA from seven UPEC (three pyelonephritis, four cystitis) isolates, three fecal/commensal strains including K-12 MG1655 was hybridized to the CFT073 microarray. Microarray data were validated using annotated K-12 and CFT073 sequences. The CFT073 genome contains 5379 genes, CGH analysis revealed that 2820 (52.4%) of these genes were common to all 11 *E. coli* strains, yet only 173 UPEC-specific genes were found in all UPEC strains by CGH but in none of the fecal/commensal strains. When the sequence of three additional sequenced UPEC strains (UTI89, 536, F11) and a commensal strain (HS) were added to the analysis, 131 genes present in all UPEC strains but in no fecal/commensal strains were identified. Ten novel genomic islands (>30 kb) were delineated by CGH in addition to the three known pathogenicity islands. These genomic islands comprise 814 kb of the 5231 kb (15.6%) genome, demonstrating the importance of horizontal transfer for UPEC. UPEC strains contain a greater number of iron acquisition systems than fecal/commensal strains, reflective of adaptation to the iron-limiting urinary tract environment. Each strain displayed distinct differences in the number and type of known virulence factors.

Further experiments conducted during the course of development of embodiments of the present invention identified a series of antigens, for example, that when conjugated to an adjuvant (e.g., cholera toxin), showed protection against infection in the kidney and bladder (See Experimental section below).

The present invention is not limited to a particular antigen. Exemplary antigens include, but are not limited to, Iha (iron-regulated gene homolog adhesin), IreA (iron-responsive element), IVIAT proteins, Hma (c2482 (novel heme-binding protein)), and cytoplasmic proteins upregulated in urine. In other embodiments, the antigen is ChuA, IroN, or IutA. In some embodiments, the proteins identified in Example 1 are utilized. Additional antigens are known to those of skill in the art. In some embodiments, one or more antigens are used in combination. The present invention is not limited to a particular combination of antigens. In some embodiments, one or more, two or more, three or more, or a larger number of antigens are administered in combination.

In some embodiments, fragments of antigens are utilized for immunization. For example, in some embodiments, extracellular domain or loops (e.g., loop 7 of IroN or loop 6 of IutA) are utilized as antigens.

In some embodiments, antigens are conjugated to adjuvants or other immune system modulators. In one exemplary embodiment, antigens are conjugated to cholera toxin. Additional adjuvants and immune system modulators are known to those of skill in the art.

An effective amount of the present vaccine is one in which a sufficient immunological response to the vaccine is raised to protect a subject exposed to bacteria in the urinary tract (e.g., *E. coli*) from contracting a UTI. Preferably, the subject is protected to an extent in which from one to all of the adverse physiological symptoms or effects (e.g., excess bacteria in the urinary tract, inflammation, and pain) of the disease to be prevented are found to be significantly reduced.

Preparation of Vaccines which Contain Protein Sequences as Active Ingredients is Generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables either as liquid solutions or suspensions; solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like, and combinations thereof. In addition, if desired, the vaccine may contain minor amounts of auxiliary substances such as wetting or emulsifying agents, pH buffering agents, or adjuvants which enhance the effectiveness of the vaccines. The protein sequences may be formulated into the vaccine as neutral or salt forms known in the art.

The vaccines are administered in a manner compatible with the dosage formulation, and in such amount as will be therapeutically effective and immunogenic. The quantity to be administered depends on the subject to be treated. The composition can be administered in a single dose, or in repeated doses. Dosages may contain, for example, from 1 to 1,000 micrograms of antigen (vaccine), but preferably do not contain an amount of bacterial-based antigen sufficient to result in an adverse reaction or physiological symptoms of infection. Methods are known in the art for determining suitable dosages of active antigenic agent.

The vaccine may be given in a single dose schedule or using a multiple-dose schedule. A multiple-dose schedule is one in which a primary course of vaccination may be with 1-10 separate doses, followed by other doses given at subsequent time intervals required to maintain and/or reinforce the immune response, for example, at 1 day to 1 year for a second dose and if needed, a subsequent dose(s) after intervals of approximately 1 day to 1 year.

The composition containing the present vaccine may be administered in conjunction with an adjuvant or with an acceptable carrier which may prolong or sustain the immunological response in the host animal. An adjuvant is a substance that increases the immunological response to the present vaccine when combined therewith. The adjuvant may be administered at the same time and at the same site as the vaccine or at a different time, for example, as a booster. Adjuvants also may advantageously be administered to the animal in a manner or at a site or location different from the manner, site or location in which the vaccine is administered. Adjuvants include aluminum hydroxide, aluminum potassium sulfate, heat-labile or heat-stable enterotoxin isolated from *Escherichia coli*, cholera toxin or the B subunit thereof, diphtheria toxin, tetanus toxin, pertussis toxin, Freund's incomplete adjuvant, Freund's complete adjuvant, and the like. Toxin-based adjuvants, such as diphtheria toxin, cholera tetanus toxin and pertussis toxin, may be inactivated prior to use, for example, by treatment with formaldehyde. Other possibilities involve the use of immunomodulating substances such as lymphokines (e.g. IFN-$\gamma$, IL-2 and IL-12) or synthetic IFN-gamma. inducers such as poly I:C in combination with the above-mentioned adjuvants.

In some embodiments, the present vaccine composition is administered directly to a subject not yet exposed to a bacterium which causes a UTI. In other embodiments, the vaccine is administered to a subject already exhibiting symptoms of a UTI. The present vaccine may be administered, for example, orally, nasally, or parenterally. Examples of parenteral routes of administration include intradermal, intramuscular, intravenous, intraperitoneal, subcutaneous and intranasal routes of administration.

When administered as a solution, the present vaccine may be prepared in the form of an aqueous solution, a syrup, an elixir, or a tincture. Such formulations are known in the art, and are prepared by dissolution of the antigen and other appropriate additives in the appropriate solvent systems. Such solvents include water, saline, ethanol, ethylene glycol, glycerol, Al fluid, etc. Suitable additives known in the art include certified dyes, flavors, sweeteners, and antimicrobial preservatives, such as thimerosal (sodium ethylmercurithiosalicylate). Such solutions may be stabilized, for example, by addition of partially hydrolyzed gelatin, sorbitol, or cell culture medium, and may be buffered by methods known in the art, using reagents known in the art, such as sodium hydrogen phosphate, sodium dihydrogen phosphate, potassium hydrogen phosphate and/or potassium dihydrogen phosphate.

Liquid formulations may also include suspensions and emulsions. The preparation of suspensions, for example using a colloid mill, and emulsions, for example using a homogenizer, is known in the art.

Parenteral dosage forms, designed for injection into body fluid systems, require proper isotonicity and pH buffering to the corresponding levels of body fluids. Parenteral formulations are generally sterilized prior to use.

Isotonicity can be adjusted with sodium chloride and other salts as needed. Other solvents, such as ethanol or propylene glycol, can be used to increase solubility of ingredients of the composition and stability of the solution. Further additives which can be used in the present formulation include dextrose, conventional antioxidants and conventional chelating agents, such as ethylenediamine tetraacetic acid (EDTA).

The present invention further provides kits comprising the vaccine compositions comprised herein. In some embodiments, the kit includes all of the components necessary, sufficient or useful for administering the vaccine. For example, in some embodiments, the kits comprise devices for administering the vaccine (e.g., needles or other injection devices), temperature control components (e.g., refrigeration or other cooling components), sanitation components (e.g., alcohol swabs for sanitizing the site of injection) and instructions for administering the vaccine.

EXPERIMENTAL

The following examples are provided in order to demonstrate and further illustrate certain preferred embodiments and aspects of the present invention and are not to be construed as limiting the scope thereof.

Example 1

Identification of Virulence Genes

This Example describes the identification of E. coli genes associate with urinary tract infections.
A. Materials and Methods
Bacterial Strains.

E. coli CFT073 was isolated from the blood and urine of a patient admitted to the University of Maryland Medical System for the treatment of acute pyelonephritis. This strain is highly virulent in the CBA mouse model of ascending UTI (Mobley et al., 1993. Molecular Microbiology 10:143-55), is cytotoxic for cultured human renal proximal tubular epithelial cells (Mobley et al., 1990. Infection & Immunity 58:1281-9) and its genome has been fully sequenced and annotated (Welch et al., 2002. Proceedings of the National Academy of Sciences of the United States of America 99:17020-4). Three collections of E. coli strains isolated from humans with appropriate clinical syndromes were used in this study.

Pyelonephritis strains (CFT204, CFT269, CFT325) were isolated from the urine or blood of patients who were admitted to the University of Maryland Medical System with acute pyelonephritis (bacteriuria of $\geq 10^5$ CFU/mL, pyuria, fever, and no other source of infection) (Mobley et al., 1993. supra). Cystitis strains (F3, F11, F24, F54) were isolated from the urine of women under the age of 30 years with first episodes of cystitis and bacteriuria of $\geq 10^5$ cfu/mL (Stapleton et al., 1991. Journal of Infectious Diseases 163:773-9). Fecal/commensal E. coli isolates (EFC4, EFC9) were collected from healthy women aged 20-50 years with no history of diarrhea, antibiotic usage or symptomatic urinary tract infection within the past month (Mobley et al., 1993. supra). Additionally, the laboratory-adapted fecal/commensal E. coli isolate K-12 MG1655 was used as a negative control for CGH microarray experiments as the full genome sequence has been determined (Blattner et al., 1997. Science 277:1453-74).

Genome Alignments of E. coli Strains CFT073 and K-12 MG1655.

The full genomes of E. coli CFT073 (90) (GenBank Accession No. AE014075) and E. coli K-12 MG1655 (8) (GenBank Accession No. U00096) were sequentially aligned in $\leq 20$ kb segments using the coliBASE software (Chaudhuri et al., Nucleic Acids Research 32:D296-9). Using a gene-by-gene comparison of these two genomes, it was possible to identify CFT073 genes that are present in K-12 but not annotated as present. Genes were classified as present if (i) the same gene was annotated in both strains, (ii) an orthologous gene was identified in K-12 or (iii) a gene with a high level of nucleotide identity to a CFT073 gene was found in K-12. Genes that were severely truncated in either strain were not considered present. The findings from this gene-by-gene comparison between the E. coli CFT073 and E. coli K-12 genomes were used to validate the microarray data.
Bioinformatic Screen of the E. coli CFT073 Genome.

Each of the coding sequences for the E. coli CFT073 genome were compared against the coding sequences for the publicly available uropathogenic E. coli genomes (UTI89, 536 and F11) as well as all other commensal and diarrheagenic E. coli listed in Table 1 using BLAST Score Ratio Analysis (BSR) (Rasko et al., 2005. BMC Bioinformatics 6:2). The comparisons in this study were performed using the nucleotide sequences for each coding region instead of the peptide coding regions to allow direct comparison between the microarray studies and the BSR analysis (Peptide comparisons were also performed and the data matches the nucleotide comparisons). For each of the predicted coding sequences (CDS) of E. coli CFT073, a BLASTN raw score was obtained for the alignment against itself (REF_SCORE) and the most similar CDS (QUE_SCORE) in each of the genomes of in Table 1. These scores were then normalized by dividing the QUE_SCORE obtained for each query genome CDS by the REF_SCORE. CDS with a normalized ratio of <0.4 were considered to be non-homologous and scored as absent in this dataset. A normalized BLAST score ratio of 0.4 is generally similar to two CDS being ~30% identical over their entire length. A normalized BLAST score ratio >0.8 indicates that the CDS are highly conserved and were scored as Present in the study. This value represents nucleotide identity of greater than ~85-90% identity over 90% of the reference sequence indicative of a highly conserved sequence. CDS labeled as divergent have BSR values between these two extremes and represent genes that have diverged but still show a significant level of similarity that they will be identified as homologs and depending on the location of the microarray probe within the gene may be identified as present or absent in that dataset.
Comparative Genomic Hybridization (CGH) Microarray Analysis.

The E. coli CFT073-specific DNA microarray (NIMBLEGEN Systems Inc., Madison, Wis.) includes 5379 ORFs from the CFT073 genome sequence (Welch et al., 2002. Proceedings of the National Academy of Sciences of the United States of America 99:17020-4). Each ORF is represented on the glass slide by a minimum of 17 unique probe pairs of 24-mer in situ-synthesized oligonucleotides. Each pair consists of a sequence perfectly matched to the ORF, and another adjacent sequence harbors two mismatched bases for determination of background and cross-hybridization, equating to 190,000 probes per array.

Total genomic DNA from log-phase UPEC and fecal/commensal E. coli isolates was isolated using Genomic-Tip 500/G columns (Qiagen) according to the manufacturer's protocol. The DNA concentration was adjusted to approximately 1 μg/μL and sent to NIMBLEGEN systems for microarray analysis using the *E. coli* CFT073-specific DNA microarray. Genomic DNA was labelled with a random prime reaction (Selzer et al., 2005. Genes Chromosomes Cancer 44:305-19). DNA (1 μg) was mixed with 1 O.D. of 5'-Cy3 labelled random nonamer (TriLink Biotechnologies) in 62.5 mM Tris-HCl, 6.25 mM MgCl2 and 0.0875% β-mercaptoethanol, denatured at 98° C. for 5 min, chilled on ice, and incubated with 100 units Klenow fragment (NEB) and dNTP mix [6 mM each in TE] for 2 h at 37° C. Reactions were terminated with 0.5 M EDTA (pH 8.0), precipitated with isopropanol, and resuspended in water. A 50-fold amplification was typically achieved. Labelled genomic DNA was hybridized to arrays in 1× NIMBLEGEN Hybridization Buffer (NIMBLEGEN systems) for 16 hours at 45° C. using a Hybwheel hybridization apparatus (NIMBLEGEN systems) in a rotisserie oven. The next morning, arrays were washed with nonstringent wash buffer (6×SSPE, 0.01% [v/v] tween-20) for 2 min, and then twice in stringent wash buffer (100 mM MES, 0.1 M NaCl, 0.01% [v/v] tween-20) for 5 min, all at 47.5° C. Finally, arrays were washed again in non-stringent wash buffer (1 min) and rinsed twice for 30 sec in 0.05×SSC. Arrays were spun dry in a custom centrifuge and stored until scanned.

Microarrays were scanned at 5 μm resolution using the GENEPIX 4000b scanner 223 (Axon Instruments, Union City Calif.), and pixel intensities were extracted using NIMBLESCAN image extraction and analysis software (NimbleGen). Data from all microarray experiments were normalized by NimbleGen using the technique described by Irizarry and colleagues (Irizarry et al., 2003. Biostatistics 4:249-64) and log 2 transformed prior to analysis. The normalized data took into account the signal intensities from every probe (perfect match and mismatch oligonucleotides) for each ORF in the genome. Normalized data were analyzed for the presence/absence of annotated open reading frames (ORFs) compared to the *E. coli* CFT073 reference strain. ORFs with normalized array values less than 7.9 were considered to be absent from the test strain compared to the reference strain, *E. coli* CFT073. The cut-off value varies between individual microarray experiments, as normalization of data from multiple experiments is dependent upon the set of input data. To validate the normalized, log 2 transformed microarray data, a gene-by-gene comparison between the *E. coli* CFT073 and *E. coli* K-12 genomes was conducted using the coliBASE software (Chaudhuri et al., 2004. Nucleic Acids Research 32:D296-9).

Serotyping and Virulence Gene Identification.

All serotyping and virulence gene identification was conducted by the Gastroenteric Disease Center at Pennsylvania State University. Using PCR, strains were tested for the presence of a range of virulence genes associated with UPEC and other *E. coli* strains: LT, Heat labile toxin; STa/STb, Heat stable toxin a,b; STX1/STX2, Shiga toxin types 1,2; CNF1/2, Cytotoxic necrotizing factor 1,2; EAE, intimin-gamma; BFP, Bundle forming pili; O157, O antigen type 157; papG allele, P-fimbrial adhesion genes (alleles I, III); SFA, S-fimbrial adhesin; focG, FIC-fimbrial adhesin.

B. Results

Selection of Strains for Comparison to *E. coli* CFT073.

Seven uropathogenic strains of *E. coli* (three pyelonephritis, four cystitis) were selected for detailed genomic comparison to *E. coli* CFT073, a pyelonephritis strain used widely for the study of UTI. Serotypes and virulence gene profiles were determined for these strains and for two fecal or commensal *E. coli* strains (Table 2). UPEC strains were represented by five O serogroups (O1, O6, O18, O25 and O75), which are among the six most common UPEC O-serogroups. Direct genomic sequence comparison was also used for three additional UPEC strains (UTI89, 536, and F11) and the well characterized commensal strain HS.

Validation of Microarray Data and Comparison of *E. coli* CFT073 with *E. coli* K-12 MG1655

Genomic DNA from the seven UPEC strains and two fecal or commensal strains was hybridized to the CFT073 microarray for the purpose of comparative genomic hybridization. To validate this technique, the signal intensities from the microarrays was compared to an evaluation of whether genes of K-12 strain MG1655 are present or absent with respect to CFT073 by direct sequence comparison. Genome alignments between CFT073 and MG1655 revealed 4025 open reading frames (ORFs) in common, either as orthologous ORFs or coding regions with substantial identity at the nucleotide level. A cut-off value for the normalized microarray data was established by comparing array data signal intensity to genome alignments. The normalized microarray value that most closely represented the presence or absence of genes in K-12 (see Materials and Methods) was determined. Array data were normalized and log 2 transformed prior to analysis. Using the established cut-off value, microarray analysis identified 3878 genes common to both K-12 and CFT073.

Of the 4025 CFT073 ORFs identified in K-12 by genome alignments, 531 of these ORFs are not annotated in K-12 (i.e., predicted to encode hypothetical proteins). Microarray data confirmed the presence of 461 of these genes (87%) in the K-12 genome sequence. Many of the genes that are present in K-12, but appeared to be absent by microarray, were either truncated genes or contained divergent nucleotide sequences that would have affected DNA hybridization to the CGH arrays. The difference in the number of genes shared between K-12 and CFT073 by genome alignment versus array data was 147 genes, indicating that only 2.7% of the genes in the array could be misclassified as absent when they are present (i.e., false negative results). Thus, 97.3% of genes were classified correctly, validating the microarray for determination of gene content among strains.

Comparative Genomic Hybridization of *E. coli* CFT073 with Uropathogenic and Fecal or Commensal *E. coli* Strains The number of genes that each *E. coli* strain had in common with CFT073, based upon microarray data, is shown in Table 3. Pyelonephritis and cystitis isolates (UPEC strains) contained similar numbers of CFT073 genes whereas the fecal or commensal strains had, on average, 100 fewer genes than the UPEC isolates; the laboratory-adapted fecal or commensal strain K-12 had approximately 300 fewer genes than the UPEC isolates. Although the UPEC isolates tended to contain more CFT073 genes than the fecal or commensal strains, this difference was not statistically significant. The number of genes that were common to all 11 *E. coli* (including CFT073 and fecal or commensal) strains was 2820, representing 52.4% of the *E. coli* CFT073 genome.

Genomic Islands Identified in *E. coli* CFT7073

The 5379 ORFs of CFT073 are classified as present or absent in the three pyelonephritis, four cystitis and three fecal or commensal *E. coli* strains. The CGH microarray analysis of eight UPEC and three fecal or commensal strains clearly revealed the presence of thirteen genomic islands of >30 kb in *E. coli* strain CFT073 (Table 4). Ten islands are newly delineated and three islands previously described (REFS) were confirmed. These large genomic islands comprise 814 kb of the 5231 kb (15.6%) of the CFT073 genome.

A new nomenclature for these presumptive pathogenicity islands has been proposed based on this analysis (Table 4). Eight of the 13 genomic islands (62%) were associated with a tRNA locus, and the majority of islands contained a phage integrase, transposase or insertion sequence at one or both boundaries of the island. The size of the islands ranged from 32-123 kb (median size of 54 kb) and 10 of the 13 (77%) islands had G+C contents that differed from that of CFT073 (50.5%) (90). Seven of the genomic islands contained one or more genes with a putative or established role in virulence (PAI, ICFT073, PAI IICFT073, PAI IIICFT073, PAI VCFT073, PAI VIICFT073, PAI XICFT073, HPICFT073), while six (PAI IVCFT073, PAI VICFT073, PAI VIIICFT073, PAI IXCFT073, PAI XCFT073, PAI XIICFT073) contained no known virulence genes. However, all of the genomic islands contained a high number of ORFs with hypothetical or putative functions (Table 4), and thus additional virulence factors are likely to exist. Phage DNA sequence is common in *E. coli* CFT073; indeed five cryptic prophage genomes have been identified in this strain, although they do not contain sufficient genetic information to produce viable phage (Welch et al, supra). Genomic islands PAI IVCFT073, PAI VICFT073, PAI VIICFT073 and PAI XCFT073 are particularly phage-rich regions of sequence. PAI VIIICFT073, PAI IXCFT073 and HPICFT073 are UPEC-specific islands (found in pyelonephritis and cystitis strains only) whereas PAI XIICFT073 is pyelonephritis-specific. Strain CFT204 has more PAIs in common with CFT073 compared to the other UPEC isolates, indicating a closer evolutionary relationship between these two strains. The presence of these thirteen CFT073 genomic islands in nine other sequenced bacterial strains was examined using coliBASE genome alignments. Eleven of the CFT073 genomic islands are not present in any of the strains studied. PAI IVCFT073 however, is present in *E. coli* E2348/69 (EPEC), *Salmonella typhi* TY2 and *Salmonella typhimurium* LT2 although differences were observed at ORFs c0933, c0944-c0946 and c0967-c0970. ORFs c0963-c0968 of PAI IVCFT073 are inverted in *E. coli* E2348/69 (EPEC) relative to the CFT073 genome. Otherwise, the gene order is conserved between strains the in the genomic island regions. HPICFT073 was identified in *E. coli* O42 (EAEC) and *Yersinia pestis* CO92, although a minor difference was observed at ORF c2425, and ORFs c2424-c2429 were annotated differently between the strains. In *Y. pestis* CO92, the corresponding region of sequence from c2424-c2429 in CFT073 is annotated as irp2 and irp1, and the same ORFs have been predicted in *E. coli* O42 (EAEC) using Glimmer. The irp1 and irp2 genes encode iron-repressible yersiniabactin biosynthesis proteins, which, along with fyuA (yersiniabactin receptor) are part of the High Pathogenicity Island (HPI) in *Yersinia* species (78).

UPEC-Specific Genes

Using CGH analysis, 2820 genes that were common to all of the UPEC and fecal or commensal strains studied were identified. To estimate the number of these genes that could be considered UPEC357 specific genes, it was investigated how many genes were present in at least a certain number of UPEC strains, but not present in any of the fecal or commensal strains including strain MG1655. In a conservative assessment, there were 173 UPEC-specific ORFs that were considered present in all eight UPEC strains (including CFT073), but in none of the fecal or commensal strains.

To determine whether we were approaching a true estimate of the number of UPEC-specific genes or whether the number would continue to fall, additional strains were included in the analysis, an analysis of three sequenced UPEC strains was included. If it is asked how many of the 173 UPEC367 specific genes are also conserved among the three additional sequenced UPEC strains, UTI89, 536 and F11, but not present in sequenced commensal strain HS, the answer is 131. Thus, 131 genes are present in all 11 UPEC strains including CFT073 but in none of the fecal or commensal strains examined.

ORFs with Hypothetical Functions Comprise Half (66/131 Genes) of These 372 UPEC-Specific Genes.

The UPEC-specific group also contained seven ORFs predicted to be involved in transcriptional regulation, nine comprise ABC transport systems (12 individual ORFs annotated as being involved in ABC transport) and the chu gene cluster involved in heme/hemoglobin utilization.

Virulence-Associated Genes in Uropathogenic *E. coli* Strains.

The prevalence of eleven virulence-associated genes or operons from CFT073 (sat, picU, tsh, iha, iroN, sitABCD, iucABCD/iutA, chuSA, hlyA and usp) were assessed in the eight UPEC and three fecal or commensal isolates (Table 5). Pyelonephritis strain CFT204 contains eight of the eleven virulence-associated genes and appears most closely related to CFT073 in terms of gene content and presences of PAIs (Table 5). The pyelonephritis strains contained the most established virulence factors 6, cystitis isolates contained a mean of 4 virulence factors and fecal/commensal strains contained a mean of only 1 (with none present in *E. coli* K-12). With respect to adhesins, nine of the ten strains in this study were shown by PCR to contain papG alleles I or III (Table 2). papG allele I was present in all of the pyelonephritis strains while allele III was seen in the majority of cystitis isolates. However, the pap gene clusters showed many genes with borderline or absent array values, indicating sequence divergence at the nucleotide level. The only gene in contrast to this observation is fimH, the fimbrial tip adhesin of type 1 fimbriae, which is present in all 10 UPEC and fecal/commensal isolates studied by CGH. The bioinformatic/BSR screen of the CFT073 genome against 14 other sequenced *E. coli* strains revealed that the fimH gene is present in 12/14 strains, with only the two enteroaggregative *E. coli* (EAEC) strains lacking the entire fim gene cluster.

As many as twelve putative fimbrial gene clusters have been identified in CFT073 (81, 90); ten chaperone-usher family fimbriae and two type IV pili. Several of these chaperone-usher pathway fimbrial gene clusters were found to be UPEC-specific by CGH, including the yad/htr/ecp genes (c0166-c0172) and ORFs c4207-c4214. In each case, the chaperone-usher genes were the most highly conserved, the adhesive tip protein was the least conserved and the minor structural subunits showed varying degrees of conservation between strains. The type IV pilin genes c2394 and c2395 were present in all four pyelonephritis isolates and one of four cystitis isolates (F11), but not in fecal/commensal strains by CGH. BSR analysis revealed that the type IV pilin genes are only present in UPEC strains 536 and F11.

With respect to iron acquisition, the enterobactin gene cluster (ent/fep genes) was present in all ten *E. coli* strains analyzed by CGH and all 14 sequenced *E. coli* strains by BSR comparisons. The yersiniabactin receptor, encoded for by the fyuA gene in *Yersinia pestis* CO92 (Parkhill et al., 2001. Nature 413:523-7), is 99.9% identical to CFT073 gene c2436 at the nucleotide level. The c2436 gene, annotated as a putative pesticin receptor precursor, is present in all seven UPEC isolates but none of the fecal/commensal strains analyzed by CGH. The BSR bioinformatics screen revealed that gene c2436 is present in the UPEC strains UTI89, 536 and F11, as well as EPEC strain E110019 and EAEC strain O42. The sitABCD operon is an iron transport system in CFT073 that was present in all three pyelonephritis isolates, ¾ cystitis isolates and one fecal/commensal strain. UPEC strains UTI89, 536 and F11, plus EAEC strain O42, contain the sitABCD operon while this iron transport system was absent from ten other *E. coli* strains. The chuS (c4307) and chuA genes (c4308), involved in heme/hemoglobin transport and binding, respectively, are present in all seven UPEC strains (three pyelonephritis and four cystitis isolates) but none of the fecal/commensal strains. The chuSA genes are present in UPEC strains UTI89, 536, and F11, EHEC strains EDL933 and Sakai, and EAEC strain 42. The chuSA genes are absent from all other *E. coli* strains examined, including the commensal strain HS and the laboratory-adapted commensal strain K-12 MG1655.

TABLE 1

Sequenced *E. coli* strains used for BLAST Score Ratio (BSR) analysis against CFT073

| Strain | Disease | GenBank Accession Number |
|---|---|---|
| CFT073 | UPEC | AE014075.1 |
| UTI89 | UPEC | CP000243.1 |
| 536 | UPEC | CP000247.1 |
| F11 | UPEC | AAJU00000000 |
| K-12 MG1655 | Lab-adapted Human Commensal | U00096.2 |
| HS | Human Commensal | AAJY00000000 |
| EDL933 | EHEC | AE005174.2 |
| Sakai | EHEC | BA000007.2 |
| 101-1 | EAEC | AAMK00000000 |
| O42 | EAEC | Sanger Center |
| E24377A | ETEC | AAJZ00000000 |
| B7A | ETEC | AAJT00000000 |
| E22 | REPEC | AAJV00000000 |
| E110019 | EPEC | AAJW00000000 |
| B171 | EPEC | AAJX00000000 |

TABLE 2

Characteristics of *E. coli* strains used in this study

| Source | Strain | Isolated from | Serotype | cnf1 | papG Allele I* | papG Allele III* | SFA | facG | Hemolysin |
|---|---|---|---|---|---|---|---|---|---|
| Pyelonephritis | CFT073 | Blood | O6:H1 | − | + | − | + | + | + |
| Pyelonephritis | CFT204 | Urine | O6:H1 | − | + | − | − | − | + |
| Pyelonephritis | CFT269 | Urine | O1:H7 | − | + | − | − | − | − |
| Pyelonephritis | CFT325 | Blood | O75:H56 | − | + | − | − | − | − |
| Cystitis | F3 | Urine | O18:H7 | + | − | + | + | − | + |
| Cystitis | F11 | Urine | O6:H31 | + | − | + | + | − | + |
| Cystitis | F24 | Urine | O18:H7 | + | − | + | + | − | + |
| Cystitis | F54 | Urine | O25:H4 | − | + | − | − | − | − |
| Fecal | EFC4 | Feces | OM:H32 | − | + | − | − | − | − |
| Fecal | EFC9 | Feces | OM:H21 | − | − | − | − | − | − |

For capsule synthesis, the kpsMT genes of CFT073 encode the ATP-binding cassette (ABC) transporter components of the group II capsule gene locus (Bliss et al., Mol Microbiol 21:221-31), have been associated with virulence in UPEC (28) and were present in a single pyelonephritis strain (CFT204). The capsule genes in both UPEC and fecal/commensal *E. coli* were diverse between strains based upon DNA hybridization to the arrays. This indicates that different strains express different capsular types. The BSR data also show that at least one of the kpsMT genes was classified as divergent or absent in all 14 sequenced *E. coli* strains.

The autotransporter tsh (also referred to as vat or haemoglobin protease) (Heimer et al., 2004. Infect Immun 72:593-7) was present in all pyelonephritis isolates and three cystitis isolates (F3, F11, F24).

The uropathogenic specific protein (usp) is encoded by gene c0133 in CFT073 and was identified in one pyelonephritis and cystitis isolate but in none of the fecal/commensal strains. Furthermore, BSR analysis supported previous studies showing the usp gene is UPEC-specific. 445 The usp gene was present in all three UPEC strains but none of the EHEC, ETEC, EPEC, REPEC, EAEC or fecal/commensal *E. coli* isolates.

TABLE 3

Number of CFT073 genes present in UPEC and fecal/commensal *E. coli* strains based on CGH microarrays

| Strain Type | Strain | No. CFT073 Genes in Common | Average ± SD* |
|---|---|---|---|
| Pyelonephritis | CFT204 | 4178 | 4198 ± 37 |
|  | CFT269 | 4241 |  |
|  | CFT325 | 4176 |  |
| Cystitis | F3 | 4245 | 4189 ± 38 |
|  | F11 | 4162 |  |
|  | F24 | 4168 |  |
|  | F54 | 4181 |  |
| Fecal/ Commensal | EFC4 | 4054 |  |
|  | EFC9 | 4101 | 4011 ± 118 |
|  | K-12 | 3878 |  |

TABLE 4

Genomic islands of >30 kb identified in E. coli CFT073 using CGH

| Island No. | ORFs in Island | Location[a] | Associated tRNA | Size (kb) | % GC[b] | Virulence Genes[c] within Island | No. Hypo. ORFs[d] | Island Name |
|---|---|---|---|---|---|---|---|---|
| 1 | c0253-c0368 | 248,670-348,353 | Asp tRNA - aspV (248,554-248,630) | 100 | 47 | cdtA (c0345) picU (c0350) | 99 | PAI III$_{cfto73}$* |
| 2 | intT-ogrK | 909,332-942,273 | — | 33 | 50 | [prophage DNA] | 34 | PAI IV$_{cfto73}$* |
| 3 | c1165-c1293 | 1,127,702-1,240,752 | Ser tRNA - serX (1,241,062-1,241,149) | 113 | 49 | mchBCDEF (c1227, c1229-c1232) sfa/F1C operon (c1237-c1247) iroNEDCB (c1250-c1254) Antigen 43 precursor (c1273) | 91 | PAI V$_{cfto73}$* |
| 4 | c1400-c1507 | 1,328,014-1,388,952 | — | 61 | 51 | [prophage DNA] | 90 | PAI VI$_{cfto73}$* |
| 5 | c1518-c1601 | 1,397,313-1,451,607 | — | 54 | 50 | [prophage DNA] sitDCBA (c1597-c1600) | 61 | PAI VII$_{cfto73}$* |
| 6 | c2418-c2437 | 2,218,378-2,250,547 | Asn tRNA - asnT (2,217,922-2,217,997) | 32 | 57 | Yersiniabactin receptor (c2436) | 18 | HPI$_{cfto73}$ * (61) |
| 7 | c2449-c2475 | 2,262,986-2,316,987 | Asn tRNA - asnW (2,262,749-2,262,824) | 54 | 53 | | 23 | PAI VIII$_{cfto73}$* |
| 8 | c2482-c2528 | 2,322,324-2,365,868 | — | 44 | 50 | | 34 | PAI IX$_{cfto73}$* |
| 9 | c3143-c3206 | 3,018,710-3,066,517 | — | 48 | 49 | [prophage DNA] | 52 | PAI X$_{cfto73}$* |
| 10 | c3385-c3410 | 3,223,002-3,255,067 | Met tRNA - mesV (3,222,311-3,222,387) | 32 | 53 | Secreted protein Hcp (c3391) ClpB protein (c3392) | 19 | PAI XI$_{cfto73}$* |
| 11 | c3556-kpsM | 3,406,498-3,529,292 | Phe tRNA - pheV (3,406,225-3,406,300) | 123 | 47 | hlyA (c3570) pap operon (c3582-c3593) iha(c3610) sat(c3619) iutA (c3623) iucDCBA (c3624-c3628) Antigen 43 precursor (c3655) kpsTM (c3697-3698) | 86 | PAI I$_{cfto73}$ (29) |
| 12 | intC-c4581 | 4,274,702-4,342,875 | SectRNA - selC (4,274,308-3,406,300) | 68 | 47 | | 76 | PAI XII$_{cfto73}$* |
| 13 | c5143-c5216 | 4,919,568-4,971,387 | Phe tRNA - pheU (4,971,585-4,971,660) | 52 | 48 | pap_2 operon (c5179-c5189) | 53 | PAI II$_{cfto73}$ (71) |

[a]Location of genomic islands relative to the E. coli CFT073 genome;
[b]% GC is the G + C content of the genomic island;
[c]Established or putative virulence factors of UPEC that are found in E. coli CFT073;
[d]CFT073 genes annotated in coliBASE;
*Presumptive PAIs named in this study.

TABLE 5

Presence of virulence-associated genes in uropathogenic and fecal/1034 commensal E. coli strains

| | Virulence Factor* | | | | | | | | | | |
|---|---|---|---|---|---|---|---|---|---|---|---|
| Strain | sat | picU | tsh | iha | iroN | sif[a] | fyuA | iuc[b] | chuSA | hlyA | usp |
| CFT204 | − | + | + | + | − | + | + | + | + | + | − |
| CFT269 | − | − | + | − | − | + | + | − | + | − | − |
| CFT325 | + | − | + | + | − | + | + | − | + | − | + |
| F3 | − | − | + | − | + | + | + | − | + | + | − |
| F11 | − | − | + | − | + | + | + | − | + | − | − |
| F24 | − | − | + | − | + | − | + | − | + | − | − |
| F54 | − | − | − | − | − | + | + | − | + | − | + |
| EFC4 | − | − | − | + | − | + | − | + | − | − | − |
| EFC9 | − | − | − | − | + | − | − | − | − | − | − |
| K-12 | − | − | − | − | − | − | − | − | − | − | − |

*Established or putative virulence factors of UPEC;
[a]sitABCD;
[b]iucABCD/iutA.

Example 2

Vaccination of Mouse Model

This Example describes the urinary tract colonization of immunized CBA/J mice 48 hr after transurethral challenge with 108 CFU of E. coli CFT073. Mice received primary immunizations of (A) 30 μg or (B) 100 μg of purified antigen (Ag) crosslinked to cholera toxin (CT), followed by two 10 μg boosts at one-week intervals. Control mice were vaccinated with CT alone. Bars indicate the median and each circle represents CFU/g of bladder or kidney from an individual mouse. The limit of detection for this assay is 200 CFU/g (dotted line).

The Results are shown in FIGS. 1A and 1B. In the first trial, 10 mice per group were vaccinated with Iha (iron-regulated gene homolog adhesin), IreA (iron-responsive element), and c2482 (novel heme-binding protein) at an initial dose of 30 μg of antigen conjugated to cholera toxin. IreA showed significant protection (P=0.02) in the bladder (2 log reduction in CFU). In a subsequent trial, the initial dose was increased to 100 μg of antigen conjugated to cholera toxin. Protection was shown in the bladder for Iha, IreA, and c2482 and in the kidney for Iha, IreA and c2482.

Example 3

Additional Antigens

Figure 2:
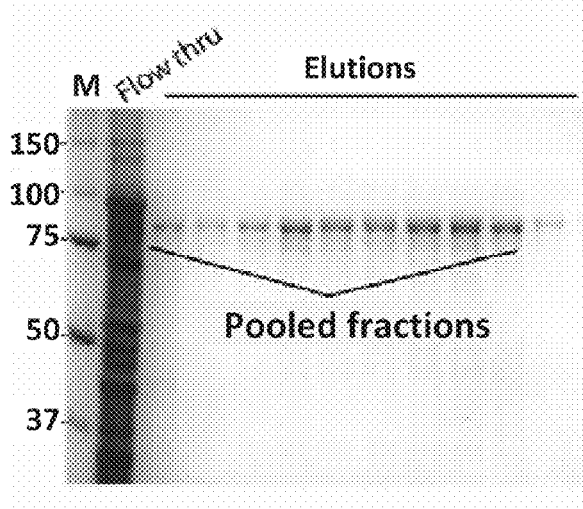
FIG. 2 shows recombinant antigen purification.
Figure 2:
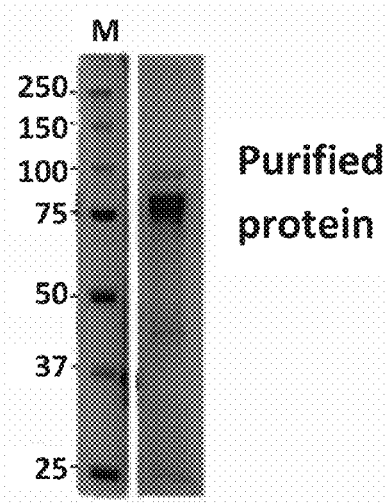

This example describes immunization of mice with additional antigens. Each protein was expressed as a fusion with a C-terminal $His_6$ tag. Proteins were isolated from outer membrane fractions by nickel-NTA column purification under denaturing conditions in the presence of 8.0 M urea. Pooled fractions containing the ~75 kDa protein of interest were dialyzed at 4° C. to remove the urea and refold the protein into PBS+0.05% Zwittergent® detergent (Calbiochem). FIG. 2 shows a schematic of the purification scheme and an SDS-PAGE gel of the purified protein.

Figure 3:
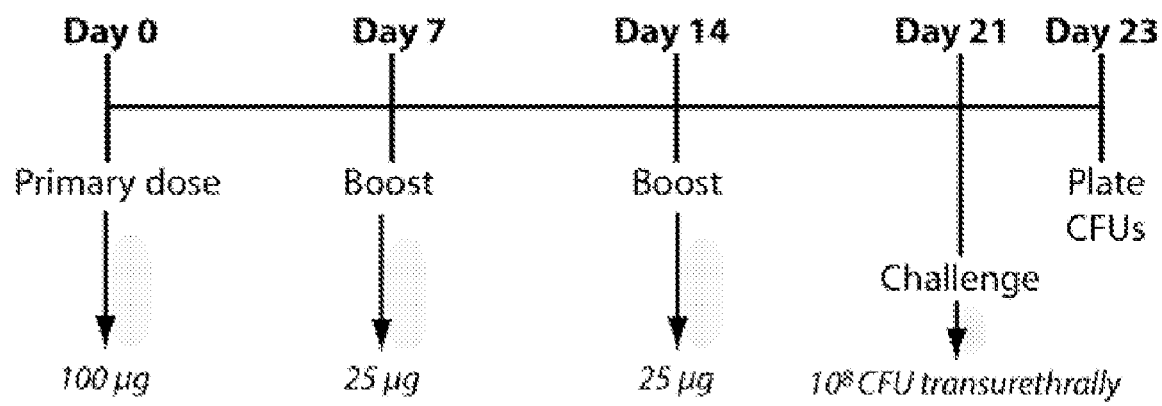
FIG. 3 shows the intranasal immunization schedule.

CBA/J mice received 100 μg of antigen intranasally, followed by two 25 μg boosts at one-week intervals. One week after the final boost, mice were transurethrally challenged with 108 CFU of *E. coli* CFT073. Protection was assessed at two days post-inoculation by culturing urinary tract tissues. All immunizations were administered intranasally (10 μl/nare) and consisted of antigen chemically crosslinked to cholera toxin at a ratio of 10:1 (antigen:adjuvant). A schematic of the vaccination schedule is shown in FIG. 3.

Figure 4:
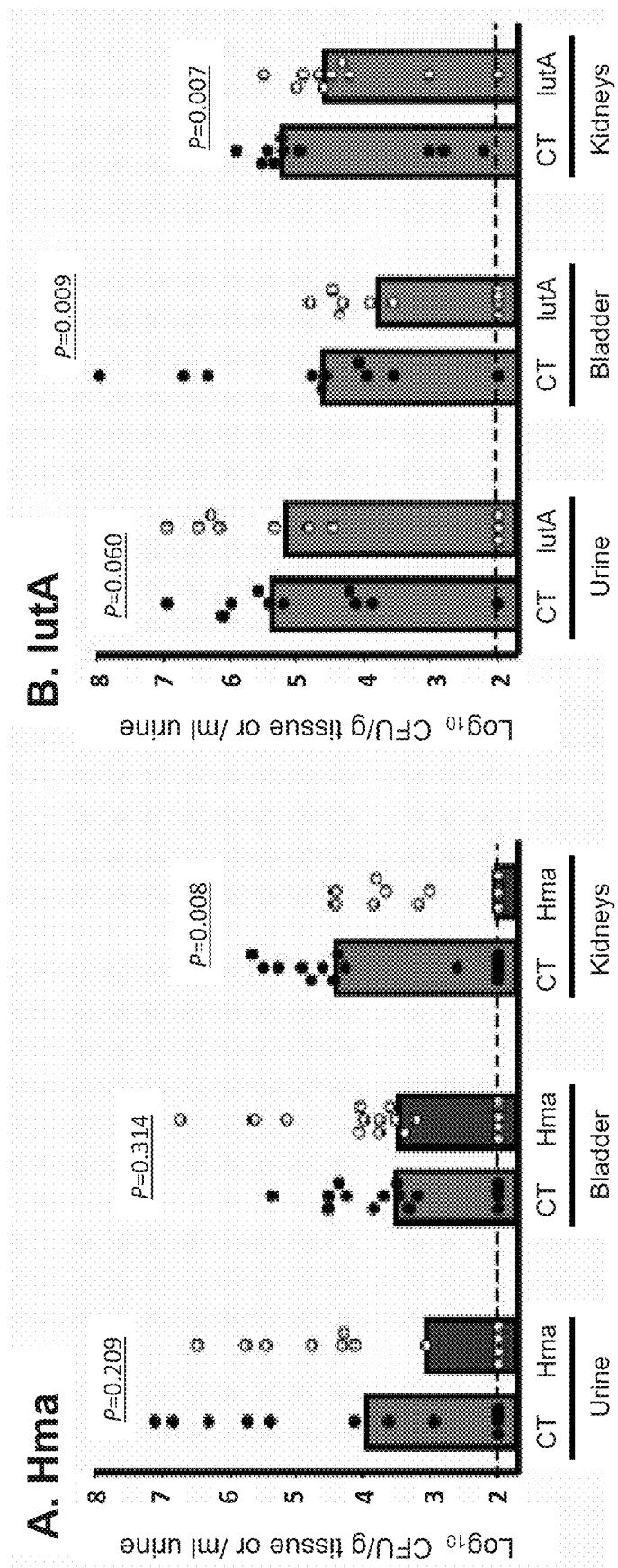
FIG. 4 shows urinary tract colonization following immunization and challenge with (A) Hma, (B) IutA, (C) IreA, (D) Iha, (E) combinations and (F) IroN and IutA peptides.
Figure 4:
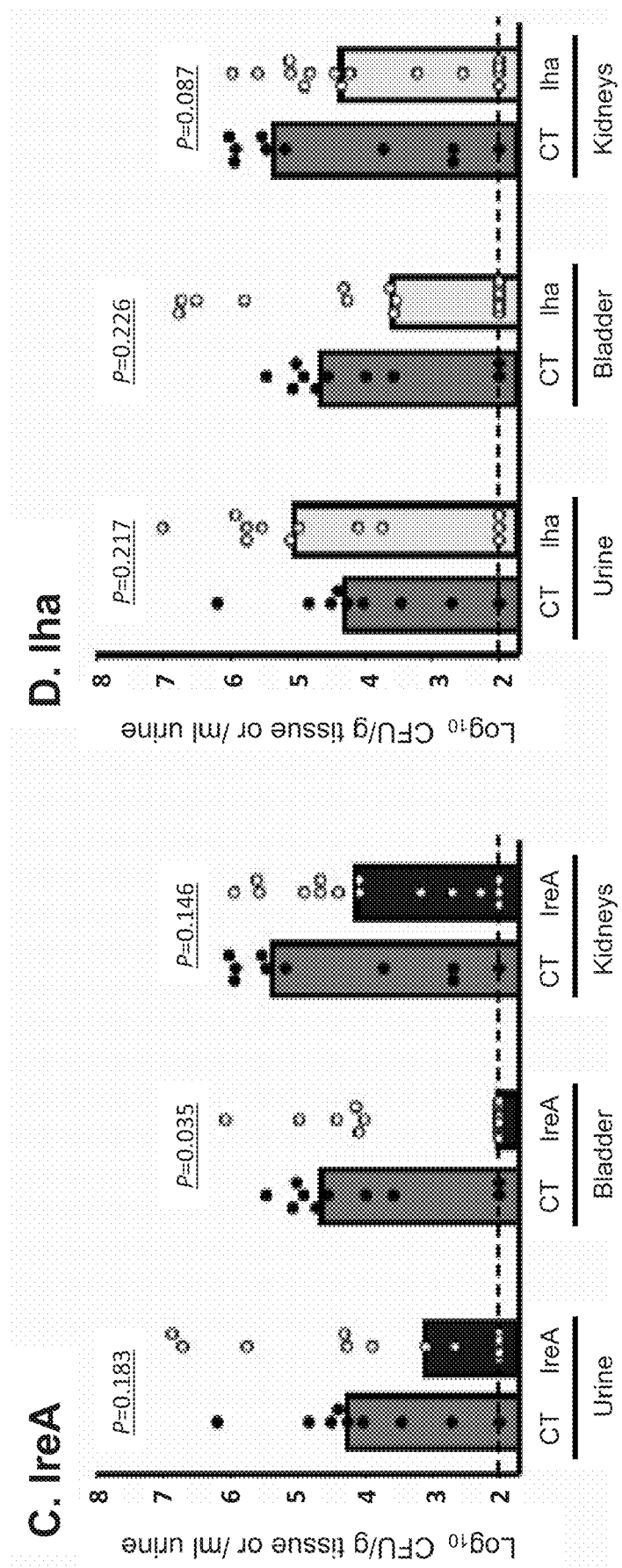
Figure 4:
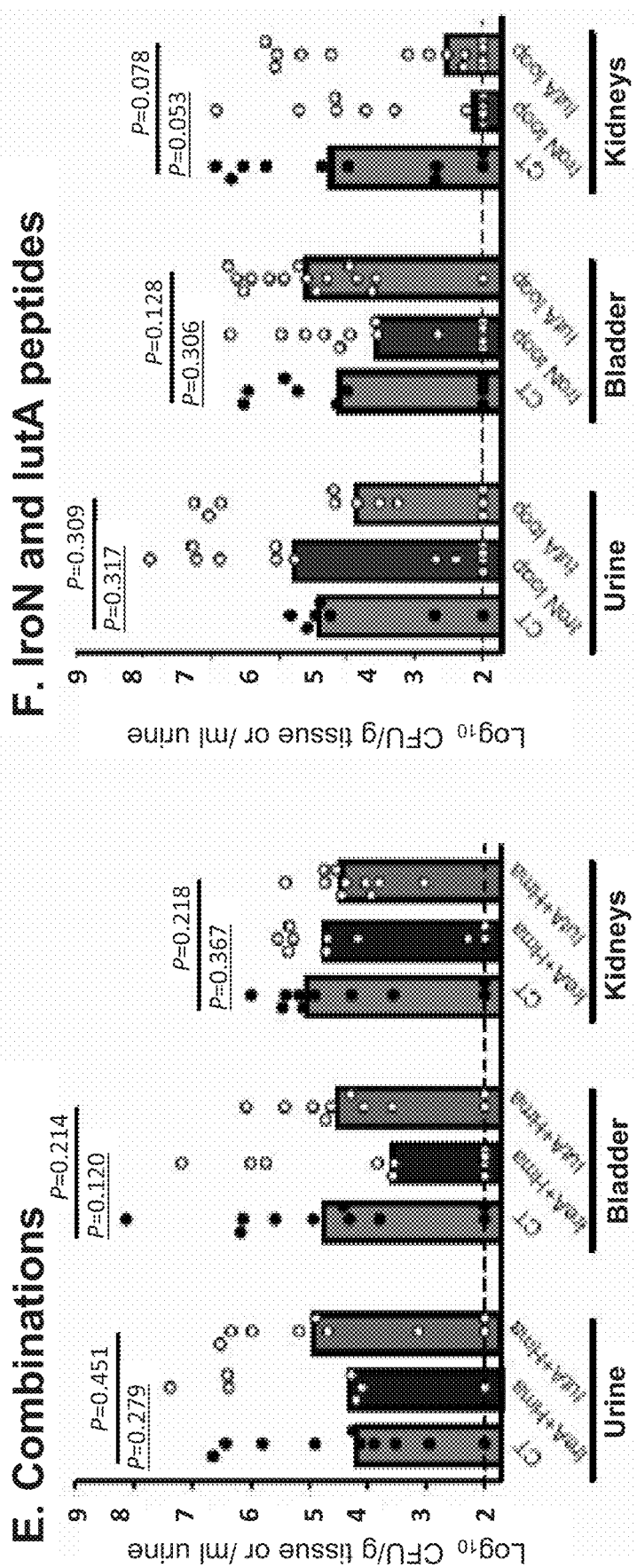

Results are shown in FIGS. 4-11. Vaccination with heme receptor Hma (c2482) or siderophore receptors IreA or IutA resulted in significantly reduced CFU levels in the urinary tract tissues of infected mice as compared to cholera toxin alone (FIG. 4 and Table 6).

Figure 5:
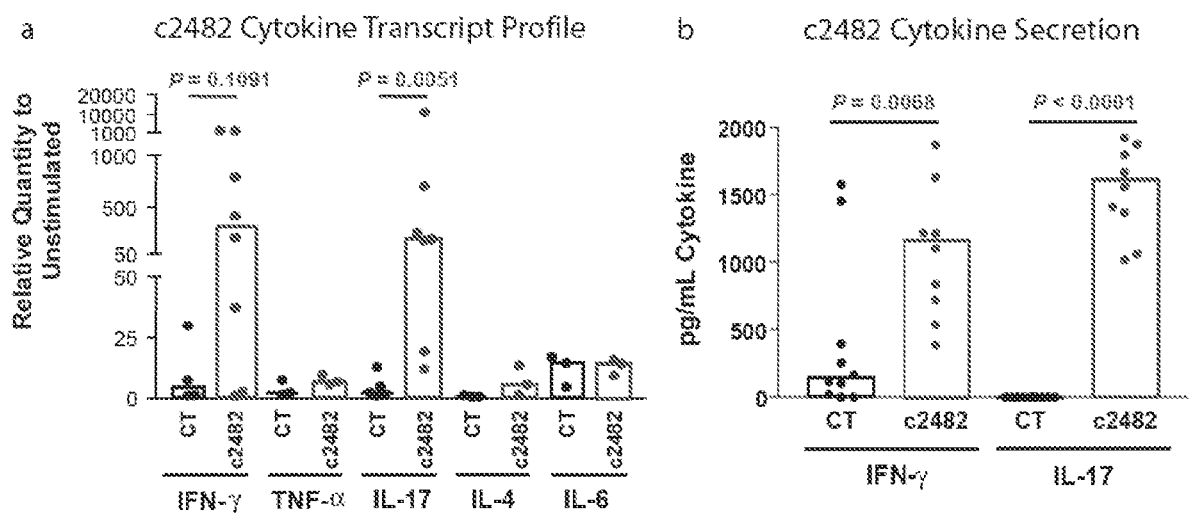
FIG. 5 shows cytokine responses of splenocytes from Hma vaccinated mice. (a) c2482 cytokine transcript profile. (b) c2482 cytokine secretion.
Figure 7:
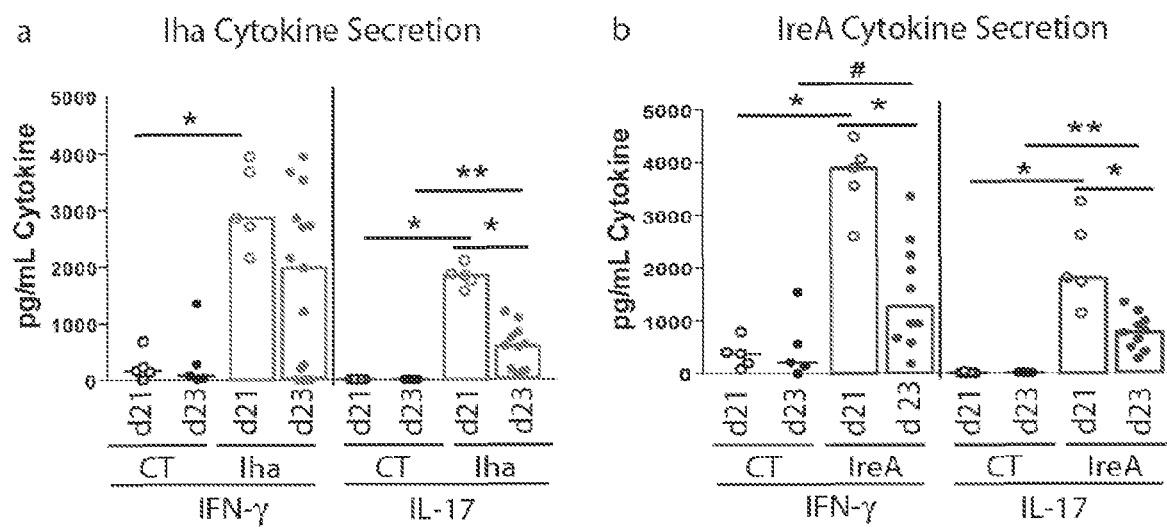
FIG. 7 shows cytokines secreted by splenocytes from Iha and IreA vaccinated mice. (a) Iha cytokine and secretion (b) IreA cytokine secretion.

The cytokine response of splenocytes from Hma-vaccinated mice was assayed. Splenocytes were harvested on day 23 and restimulated with 1 μg/mL Hma (c2482) in vitro for 6 hours before RNA was isolated for analysis by quantitative real time PCR (qPCR) or 48 hours before supernatants were collected for quantitation by two-site enzyme immunosorbant assay (ELISA). Splenocytes from immunized mice produce the cytokines IFN-γ and IL-17 when re-stimulated with the antigen (FIG. 5). FIG. 7 shows IFN-γ and IL-17 secreted by splenocytes from Iha- and IreA-vaccinated mice. Splenocytes were harvested on days 21 and 23 (post-vaccination, pre- and post-challenge) and restimulated with 1 μg/mL Iha or IreA in vitro for 48 hours before supernatants were collected for quantitation by ELISA.

Figure 6:
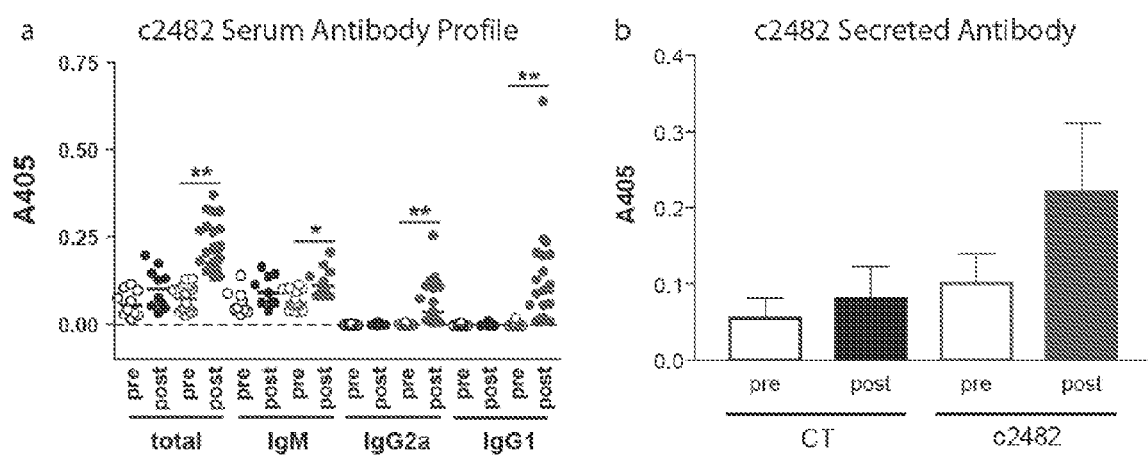
FIG. 6 shows antigen specific antibody response of Hma vaccinated mice. (a) c2482 serum antibody profile. (b) c2482 secreted antibody.
Figure 8:
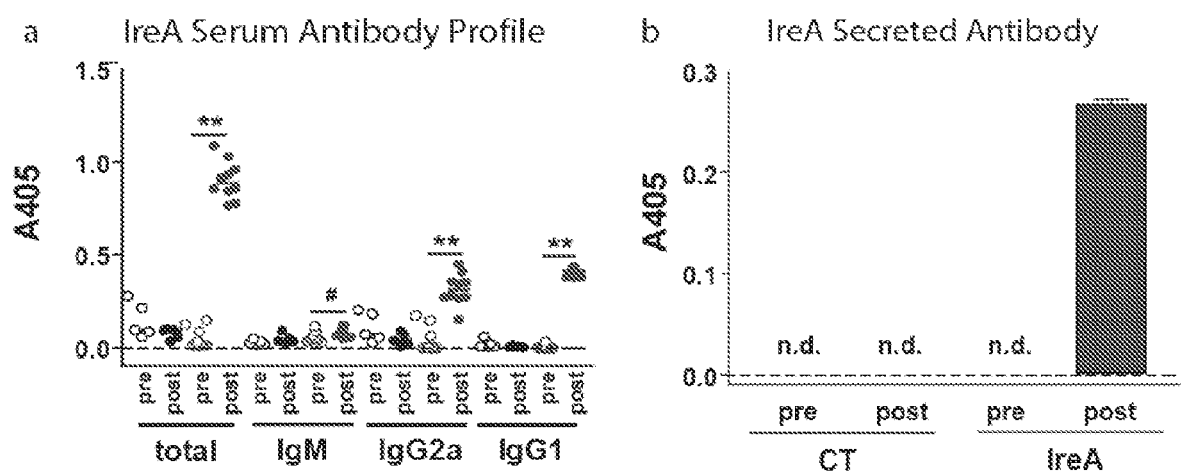
FIG. 8 shows antigen-antibody responses of IreA vaccinated mice. (a) IreA serum antibody profile. (b) IreA secreted antibody.
Figure 9:
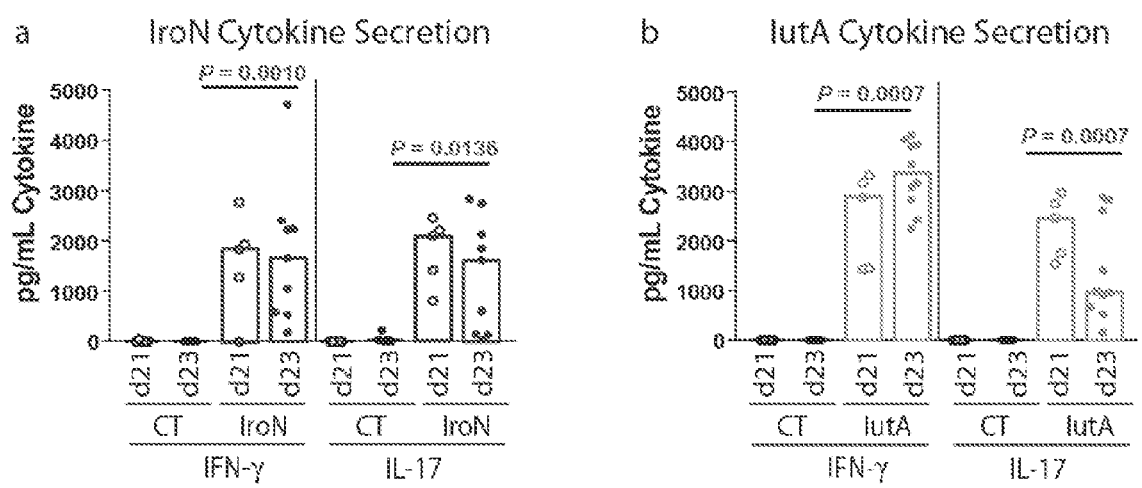
FIG. 9 shows cytokines secreted by splenocytes from peptide vaccinated mice. (a) IroN cytokine secretion and (b) IutA cytokine secretion.
Figure 10:
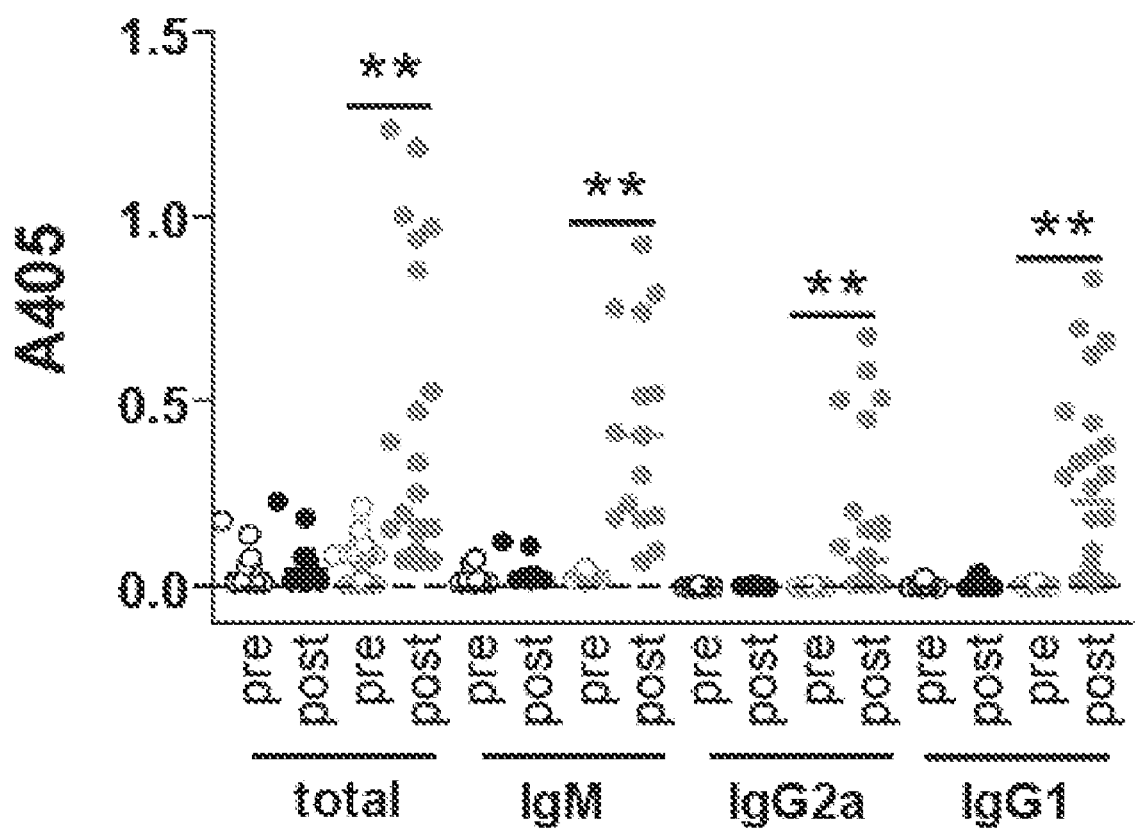
FIG. 10 shows antigen specific antibody responses of peptide vaccinated mice.

Antibody responses of vaccinated mice were also assayed. Sera and urine were collected from pre-vaccination (pre) and on day 21 (post). ELISA plates were coated with 5 μg/mL Hma (c2482) and sera was added at a 1:128 dilution. Hma-specific antibodies were detected with isotype specific antibodies conjugated to alkaline phosphatase (AP). Each dot indicates an individual animal and bars represent the median. **$P<0.0001$, *$P<0.01$. ELISA plates were coated with 10 μg/mL Hma and pooled mouse urine was added. Hma-specific antibodies were detected with an IgA-specific secondary antibody conjugated to AP. Vaccinated mice also produce increased IgM, IgG2a, IgG1 and IgA (FIG. 6). FIG. 8 shows antigen specific antibody responses of IreA vaccinated mice. Sera and urine were collected pre-vaccination (pre) and on day 21 (post). ELISA plates were coated with 5 μg/mL IreA and mouse sera was added at 1:128 dilution. Ire-A-specific antibodies were detected with isotype specific antibodies conjugated to AP. ELISA plates were coated with 10 μg/mL IreA and pooled mouse urine was added. IreA-specific antibodies were detected with an IgA-specific secondary antibody conjugated to AP.

Additionally, synthetic 30-mer peptides were generated that correspond to putative extracellular loop 7 of IroN and loop 6 of IutA. Each was used to immunize CBA/J mice. Splenocytes were harvested on days 21 and 23 (post-vaccination, pre- and post-challenge) and restimulated with 10 μg/mL IroN peptide or IutA peptide in vitro for 48 hours before supernatants were collected for quantitation by ELISA. Protection from infection was seen in the kidneys of infected animals.

Figure 11:
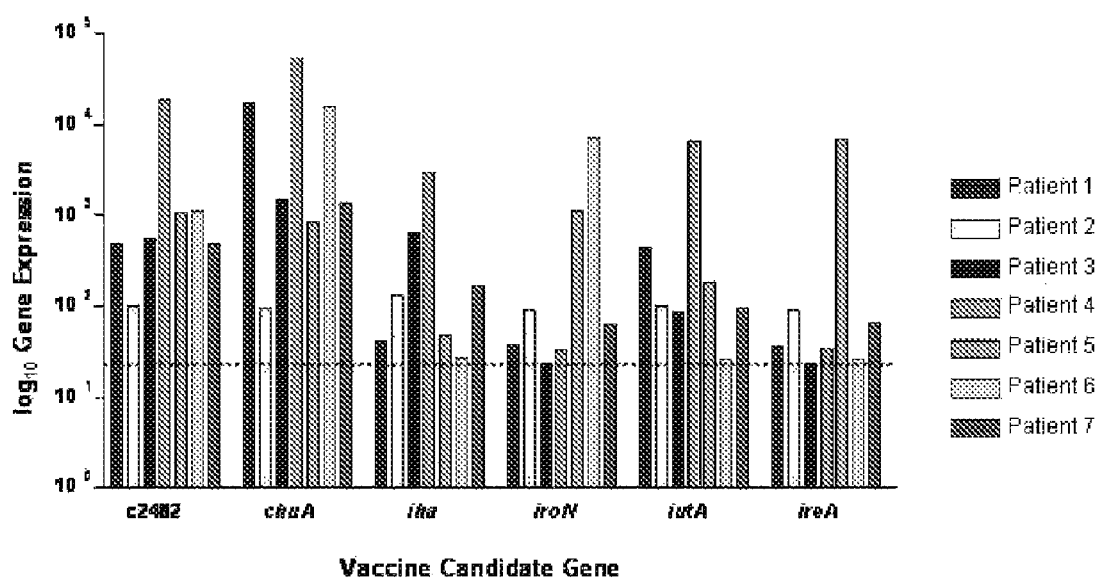
FIG. 11 shows gene expression of vaccine candidate antigens in E. coli strains during an active UTI.

FIG. 11 shows gene expression of Vaccine Candidate Antigens in *E. coli* strains during an active UTI. Urine was collected from patients visiting a urology clinic for symptoms of UTI. RNA was immediately stabilized just after collection. Bacteria (identified as *E. coli*) were harvested by centrifugation and RNA was isolated and converted to cDNA. Labeled cDNA was hybridized to an *E. coli* CFT073 microarray in triplicate.

Together, these data indicate that outer membrane iron receptors of UPEC represent vaccine targets to protect against UTI.

TABLE 6

Summary of urinary tract colonization levels following immunization with indicated vaccine and challenge with *E. coli* CFT073.

| Vaccine (n) | Urine | | Bladder | | Kidneys | |
| --- | --- | --- | --- | --- | --- | --- |
| | median CFU/ml[a] | P-value[b] | median CFU/g[a] | P-value[b] | median CFU/g[a] | P-value[b] |
| Hma (20) | $1.16 \times 10^3$ | 0.2089 | $2.91 \times 10^3$ | 0.3138 | $1.00 \times 10^2$ | 0.0084 |
| CT[c] (15) | $9.90 \times 10^3$ | | $3.22 \times 10^3$ | | $2.54 \times 10^4$ | |
| IreA (15) | $1.23 \times 10^3$ | 0.1833 | $1.00 \times 10^2$ | 0.0348 | $1.24 \times 10^4$ | 0.1459 |
| Iha (15) | $1.15 \times 10^5$ | 0.2170 | $3.75 \times 10^3$ | 0.2263 | $2.26 \times 10^4$ | 0.0869 |
| CT (10) | $1.81 \times 10^4$ | | $4.55 \times 10^4$ | | $2.30 \times 10^5$ | |
| IutA (20) | $9.98 \times 10^2$ | 0.0598 | $3.43 \times 10^3$ | 0.0088 | $2.65 \times 10^4$ | 0.0067 |
| CT (20) | $2.49 \times 10^4$ | | $4.02 \times 10^4$ | | $1.73 \times 10^5$ | |
| IroN peptide (14) | $6.06 \times 10^4$ | 0.3170 | $3.82 \times 10^3$ | 0.3085 | $1.76 \times 10^2$ | 0.0529 |
| IutA peptide (15) | $7.13 \times 10^3$ | 0.3090 | $3.97 \times 10^4$ | 0.1277 | $3.34 \times 10^2$ | 0.0782 |
| CT (10) | $2.52 \times 10^4$ | | $1.22 \times 10^4$ | | $1.68 \times 10^4$ | |
| Hma + IreA (10) | $1.90 \times 10^4$ | 0.2790 | $3.65 \times 10^3$ | 0.1200 | $5.11 \times 10^4$ | 0.3667 |

TABLE 6-continued

Summary of urinary tract colonization levels following immunization with indicated vaccine and challenge with E. coli CFT073.

| Vaccine (n) | Urine | | Bladder | | Kidneys | |
|---|---|---|---|---|---|---|
| | median CFU/ml[a] | P-value[b] | median CFU/g[a] | P-value[b] | median CFU/g[a] | P-value[b] |
| Hma + IutA (10) | $7.94 \times 10^4$ | 0.4512 | $3.15 \times 10^4$ | 0.2135 | $2.63 \times 10^4$ | 0.2179 |
| CT (10) | $1.60 \times 10^4$ | | $5.72 \times 10^4$ | | $1.09 \times 10^5$ | |

[a]The limit of detection for CFU/g or /ml determination is $1.00 \times 10^2$.
[b]Significance was determined using the one-tailed Mann-Whitney test.
[c]Cholera toxin adjuvant control.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields are intended to be within the scope of the following claims.

What is claimed is:

1. A method of inducing an immune response, comprising administering a composition comprising an effective amount of at least a portion of one or more isolated antigens selected from the group consisting of Iha, IreA, IutA and c2482 to a subject under conditions such that said subject generates an immune response to E. coli in said subject's urinary tract.

2. The method of claim 1, wherein said composition further comprises an adjuvant.

3. The method of claim 2, wherein said adjuvant is cholera toxin.

4. The method of claim 3, wherein said cholera toxin is crosslinked to said antigen.

5. The method of claim 1, wherein said immune response protects said subject from developing symptoms of a urinary tract infection.

6. The method of claim 1, wherein said subject exhibits decreased levels of bacteria in said subject's bladder or kidney.

7. The method of claim 1, wherein said at least a portion is a peptide that includes extracellular loop 6 of IutA.

8. A method of preventing urinary tract infections by E. coli in a subject, comprising administering a composition comprising an effective amount of at least a portion of one or more isolated antigens selected from the group consisting of Iha, IreA, IutA and c2482 to a subject under conditions such that said subject does not develop symptoms of a urinary tract infection caused by E. coli.

9. The method of claim 8, wherein said subject exhibits decreased levels of bacteria in said subject's bladder or kidney.

10. The method of claim 9, wherein said bacteria is E. coli.

11. The method of claim 8, wherein said composition further comprises an adjuvant.

12. The method of claim 11, wherein said adjuvant is cholera toxin.

13. The method of claim 12, wherein said cholera toxin is crosslinked to said antigen.

14. The method of claim 8, wherein said at least a portion is a peptide that includes extracellular loop 6 of IutA.

15. The method of claim 1, wherein said composition further comprises an effective amount of at least a portion of IroN.

16. The method of claim 15, wherein said at least a portion of IroN is a peptide that includes extracellular loop 7 or IronN.

17. The method of claim 8, wherein said composition further comprises an effective amount of at least a portion of IroN.

18. The method of claim 17, wherein said at least a portion of IroN is a peptide that includes extracellular loop 7 or IronN.

* * * * *